United States Patent
Ochoa et al.

(10) Patent No.: US 6,206,929 B1
(45) Date of Patent: *Mar. 27, 2001

(54) BIPOLAR HIP PROSTHESIS WITH LOCKING HEAD

(75) Inventors: Jorge Ochoa, Norton; Farid Bruce Khalili, Chestnut Hill, both of MA (US)

(73) Assignee: Depuy Orthopaedics, Inc., Warsaw, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/049,452

(22) Filed: Mar. 27, 1998

(51) Int. Cl.[7] .................................................. A61F 2/34
(52) U.S. Cl. .................................... 623/22.17; 623/22.26
(58) Field of Search ................................ 623/22, 23, 19

(56) References Cited

U.S. PATENT DOCUMENTS

| | | |
|---|---|---|
| 3,813,699 | 6/1974 | Giliberty . |
| 3,863,273 | 2/1975 | Averill . |
| 4,044,403 * | 8/1977 | D'Errico .............................. 623/23 |
| 4,172,296 * | 10/1979 | D'Errico .............................. 623/22 |
| 4,241,463 | 12/1980 | Khovaylo . |
| 4,770,658 | 9/1988 | Geremakis .......................... 623/22 |
| 4,798,610 | 1/1989 | Averill et al. ....................... 623/22 |
| 5,156,626 | 10/1992 | Broderick et al. .................. 623/22 |
| 5,263,988 | 11/1993 | Huebner ............................. 623/22 |

FOREIGN PATENT DOCUMENTS

| | | | |
|---|---|---|---|
| 0 208 578 A1 * | 1/1987 | (EP) | ..................................... 623/22 |
| 0 412 438 A2 * | 2/1991 | (EP) | ..................................... 623/22 |
| 2 583 634 A1 * | 12/1986 | (FR) | ..................................... 623/23 |
| 2 701 206 A1 * | 8/1994 | (FR) | ..................................... 623/23 |
| 1-300949 * | 12/1989 | (JP) | ..................................... 623/22 |
| 4-44756 * | 2/1992 | (JP) | ..................................... 623/22 |
| 8-651 * | 1/1996 | (JP) | ..................................... 623/22 |

* cited by examiner

*Primary Examiner*—David H. Willse
(74) *Attorney, Agent, or Firm*—Nutter, McClennen & Fish, LLP

(57) ABSTRACT

An articulating prosthesis includes a cup having a shell and a liner and at least one resilient locking element. The shell has a spherical outer surface that may be adapted to articulate with an acetabulum and the liner has a spherical inner surface that forms an articulation surface for the spherical head of a stem member. The resilient locking member extends inward toward a longitudinal axis of the cup and at least partially in a superior direction. The resilient locking element defines a nominal first diameter expandable to a larger second diameter in response to a force and is returnable to the first diameter in the absence of the force for securing the head of a stem prosthesis member.

22 Claims, 2 Drawing Sheets

BIPOLAR HIP PROSTHESIS WITH LOCKING HEAD

CROSS-REFERENCE TO RELATED APPLICATION

Not Applicable.

STATEMENT REGARDING FEDERALLY SPONSORED RESEARCH

Not Applicable.

FIELD OF THE INVENTION

The present invention relates to an articulating prosthesis having a locking element.

BACKGROUND OF THE INVENTION

In a hip hemiarthroplasty procedure, the proximal portion of a femur is replaced with a suitable prosthetic hip joint implant or implant assembly that articulatably mates directly with a patient's natural acetabulum. Two types of femoral prostheses are typically suitable for hip hemiarthroplasty procedures. One type is a bipolar prosthesis. In general, a bipolar hip prosthesis, such as disclosed in U.S. Pat. Nos. 3,813,699 and 3,863,273, includes a shell having an external surface which articulates with a patient's acetabulum and an internal surface which articulates with the spherical head member of a prosthetic femoral component. The other type of prosthesis is often referred to as a unipolar endoprosthesis in which the prosthetic femoral component includes a spherical head member which is large enough to articulate directly with the acetabulum.

One drawback to the successful use of bipolar hip prostheses is that they may become displaced after insertion. In particular, the spherical head of the femoral component may become dissociated from the shell. Such a dissociation may occur as the result of the abnormal twisting of a leg, or after a trauma such as a fall, such as might cause a dislocation in a natural hip joint. A problem with some prior art bipolar hip prostheses is that, in these situations, the dissociation can only be cured by further surgery.

U.S. Pat. No. 4,798,610 describes a bipolar femoral hip prosthesis having a floating locking ring that attempts to provide improvements over U.S. Pat. No. 4,241,463. According to its disclosure, the spherical head of this femoral prosthesis does not dislocate from the shell. Rather, in response to forces that would dislocate a natural hip, the shell disengages from the acetabulum. The dislocation may then be corrected in a manner similar to the manner in which the dislocation of a natural hip is corrected.

Dissociation of the components within the acetabulum is not necessarily preferred however. When correcting such a dissociation, it can be difficult to properly align the shell during correction. Also, dissociation of the components within the acetabulum and correction of such a condition can result in damage to the patient's natural bone. In addition, proper orientation of a floating locking ring, such as those described in U.S. Pat. Nos. 4,241,463 and 4,798,610, can be problematic, even during normal use of the prosthesis.

SUMMARY OF THE INVENTION

The present invention provides an articulating prosthesis having a cup and at least one resilient locking element. The cup includes a shell having a spherical outer surface shaped so as to articulate with a natural acetabulum and has a superior apex and an inferior aperture. A liner is provided on the inner surface of the shell. The liner, which may be formed from a polymeric material such as ultra high molecular weight polyethylene, has a spherical inner surface. The locking element is resilient and is disposed at least partially within the shell. The locking element extends inward, toward a longitudinal axis of the cup, and at least partially in a superior direction toward the apex of the cup.

The locking element deforms, in response to an insertion force directed from the inferior aperture from a first position, defining a first nominal diameter, outward and away from the longitudinal axis of the cup to define a second, larger diameter. When the insertion force is removed, the resilient locking member returns to its original position. An end of the locking element may define a surface portion on a projection of the spherical inner surface of the liner when the locking element is in its first position.

The articulating prosthesis may also include a stem member having a spherical head adapted to fit within and articulate with the spherical inner surface of the liner. The spherical head is sized so as to deform the locking element from its first position to its second position in response to an insertion force applied to the spherical head from an inferior direction, allowing the spherical head to pass through the second, larger diameter of the locking element and to articulatably engage the spherical inner surface of the liner. The spherical head is also sized so as to allow the resilient locking element to return to its first, nominal diameter after the spherical head has engaged the inner surface of the liner.

BRIEF DESCRIPTION OF THE DRAWINGS

The invention will be more fully understood by reference to the following detailed description when considered in conjunction with the accompanying drawings, in which.

DETAILED DESCRIPTION OF THE INVENTION

Figure 1:
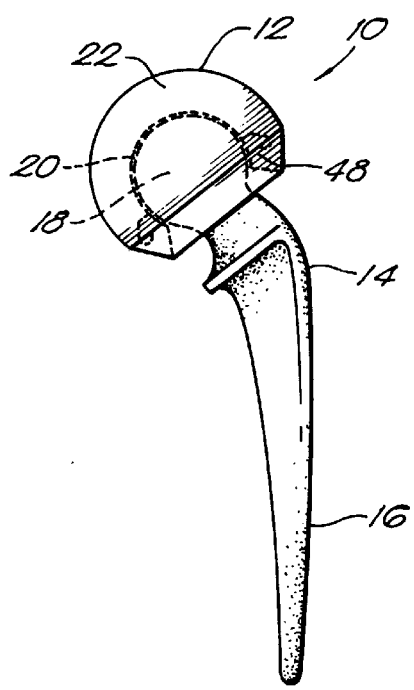
FIG. 1 is a side view of an articulating prosthesis of the invention having an articulating cup and an endoprosthesis component.

An articulating prosthesis 10 of the invention is illustrated in FIG. 1 as an articulating cup 12 in association with a proximal femoral endoprosthesis 14. The endoprosthesis 14 includes a stem portion 16 which is received within the medullary canal of a femur and a spherical head 18 which is articulatably matable with the articulating cup 12. The articulating cup 12 has a spherical inner surface 20 which is articulatably matable with the spherical head 18 and a substantially spherical outer surface 22 which is articulatably matable with a natural acetabulum.

Figure 2:
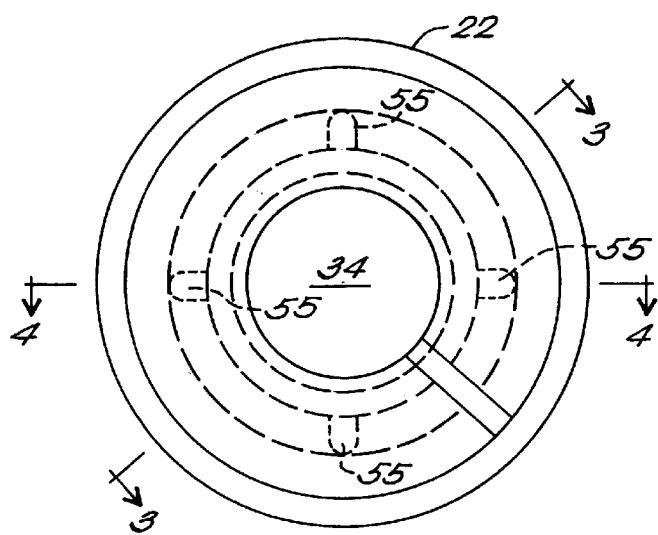
FIG. 2 is an inferior view of an articulating cup of the invention.
Figure 3:
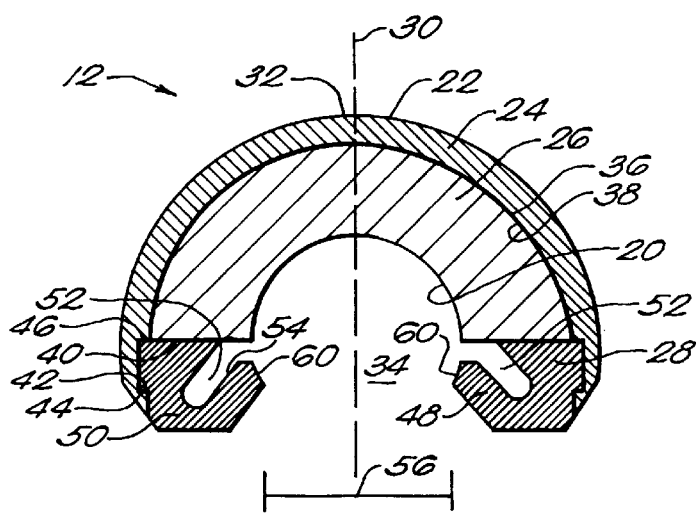
FIG. 3 is a cross sectional view of the cup of FIG. 2 taken along line 3—3.
Figure 4:
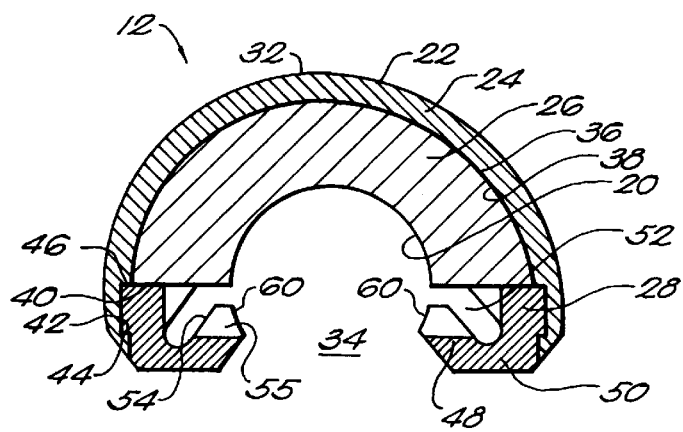
FIG. 4 is a cross sectional view of the cup of FIG. 2 taken along line 4—4.

As shown in FIGS. 2 to 4, the articulating cup 12 may be provided in several distinct pieces including a shell 24, a liner 26 and a locking liner portion 28. The cup 12 also includes a longitudinal axis 30, a superior apex 32 and an inferior aperture 34. The shell 24 is preferably formed from a biocompatible metal such as titanium, a titanium alloy or a stainless steel, and has an inner surface 36 and a spherical outer surface 22 adapted to articulate with a natural acetabulum. The outer surface 22 of shell 24 should be sized according to the size of the patent's acetabulum, and generally will have a diameter between about 36 and 80 millimeters.

The liner 26 is preferably formed from a polymeric material, such as ultra high molecular weight polyethylene. The liner 26 has an outer surface 38, which matable to the inner surface 36 of the shell 24. The liner 26 also has a spherical inner surface 20 which is suited to articulate with the spherical head 18 of a femoral endoprosthesis 14. Preferably, the spherical inner surface 20 of the liner 26 covers no more than one half of a sphere. In the embodiment of FIGS. 3–4, the inner surface 20 of the liner 26 is hemispherical and the liner 26 is seated wholly within the shell 24.

The locking liner portion 28 may also be formed from a polymeric material such as ultra high molecular weight polyethylene. As shown in FIGS. 3–4, the locking liner portion 28 has a superior surface 40 that abuts the liner 26 within the shell 24. The locking liner portion 28 also has an inferior-facing, circumferential ledge 42 which abuts a similar, circumferential opposed ledge 44 provided on the inner surface 38 of the shell 24 proximate to the inferior aperture 34. The interlocking of the ledges 42, 44 secures the locking liner portion 28 against dissociation from the shell 24. In the embodiment of FIGS. 3 and 4, a portion of the superior surface 40 of the locking liner portion 28 also abuts an inferior facing ledge 46 on the inner surface 38 of the shell 24. In this embodiment, the locking liner portion 28 remains in its intended position and orientation within the shell 24 even if, for some reason, the liner 26 does not.

As shown in FIGS. 3 and 4, a locking element 48 extends from the locking liner portion 28. The locking element 48 is disposed around the periphery of the locking liner portion 28 proximate to the inferior aperture 34 of the cup 12 and extends inward, toward the longitudinal axis 30 of the cup 12, and in a superior direction toward the superior apex 32 of the cup 12.

In the disclosed embodiments, the locking element 48 extends from the liner locking portion 28, however, a person of ordinary skill in the art will recognize that other configurations are possible in keeping with the spirit of the invention. For example, the liner 26 and the liner locking portion 28 could be provided as a single element with the locking element 48 extending from the combined liner. Generally, the locking element 48 preferably extends from a region 50 adjacent to the shell 24 and in proximity to the inferior aperture 34. In addition, the locking element 48 need not be disposed continuously around the periphery of the inferior aperture 34, but may consist of a plurality of discrete locking elements.

The locking element 48 is resilient and may be deformed in response to an insertion force directed from the inferior aperture 34 towards the superior apex 32, such as the insertion force provided by the insertion of the spherical head 18 of a femoral endoprosthesis 14 into the inferior aperture 34 of the cup 12. A peripheral groove 52 may be disposed on the superior side 54 of the locking element 48 to provide clearance for the locking element 48 to deform. Longitudinal grooves 55 may also be provided to aid in the deforming of the locking element 48.

Figure 5:
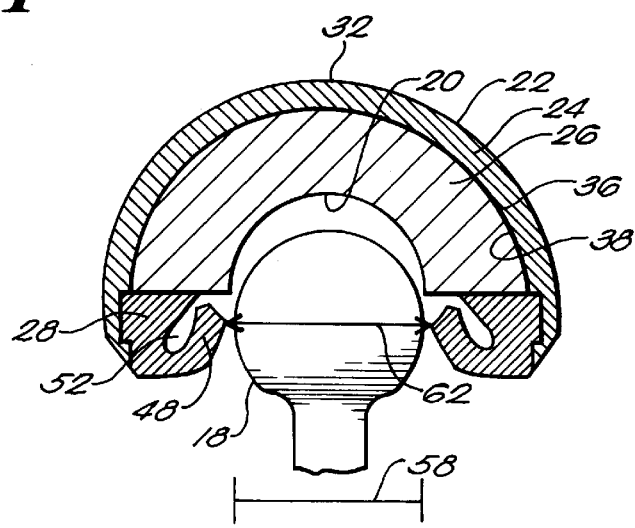
FIG. 5 is an exploded view of a spherical head of an endoprosthesis component partially inserted into the articulating cup of FIG. 2.
Figure 6:
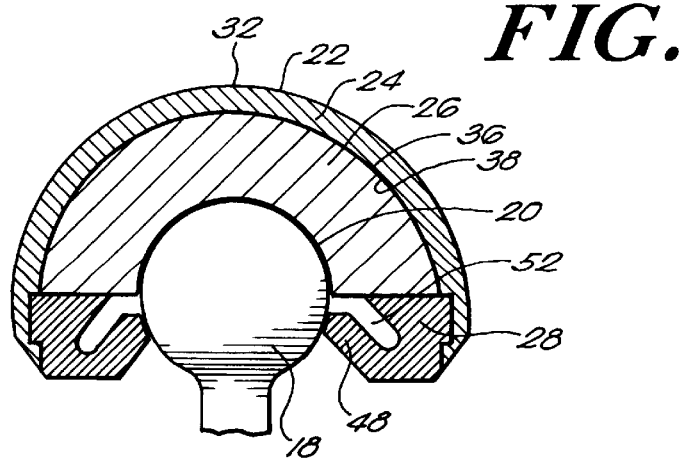
FIG. 6 is an exploded view of the spherical head and articulating cup of FIG. 5 with the head fully inserted.

In response to an insertion force, the locking element 48 deforms from a first position (FIGS. 3 and 4) defining a first nominal diameter 56, outward and away from the longitudinal axis 30 of the cup 12 to define a second, larger diameter 58 (FIG. 5). The resilient locking element 48 then returns to its first position upon removal of the insertion force, such as when the spherical head 18 of a femoral endoprosthesis has been inserted past the locking element 48 to engage the spherical inner surface 20 of the liner 26 (FIG. 6).

A head contacting portion 60 of the locking element 48 may be a spherical surface portion that, when the locking element is in its first position, defines a surface portion on a projection of the spherical inner surface 20 of the liner 26. In this way, the head contacting portion 60 will contact the spherical head 18 along a contact region. A person of ordinary skill in the art will understand, however, that other head contacting portion 60 configurations may be used, included including a rounded contacting portion (not shown) that contacts the spherical head 18 only at a point, or along a line around the periphery of the inferior aperture 34.

Generally, the spherical head 18 will have a diameter 62 between about 22 and 32 millimeters. The first nominal diameter 54 is smaller than the diameter 62 of the spherical head 18, but the locking element 48 deforms to a second, larger diameter 56 that is at least as large as the diameter 62 of the spherical head 18. In this way, the head 18 deforms the locking element 48 upon insertion into the cap 12, passes through the locking element 48, and articulatably engages the inner surface 20 of the liner 26 as the locking element 48 returns to its original position.

Once the spherical head 18 is fully inserted into the cup 12 and the locking element 48 returns to its original position, the head contacting portion 60 of the locking element 48 contacts the spherical head 18 to keep the spherical head 18 in contact with the spherical inner surface 20 of the liner 26 and to prevent dissociation of the head 18 from the cup 12. Should dissociation occur, the head 18 may be reinserted into the cup 12 by properly orienting the head 18 and providing an insertion force to push the head 18 through the locking element 48 as shown in FIGS. 5 and 6. Due to the structure of the locking element 48 of the invention, the insertion force required to insert or reinsert the head 18 into the cup 12 is less than the subluxation force required to dissociate the head 18 from the cup 12—making the head 18 difficult to dissociate from the cup 12, but making it easy to reinsert the head 18 should dissociation occur.

Although the present invention is described with respect to particular embodiments and features and uses, numerous variations or equivalents are possible without taking away from the spirit or scope of the claimed invention. All references cited herein are expressly incorporated by reference in their entirety.

What is claimed is:

1. An articulating hemiarthroplasty prosthesis comprising:
   a shell having a spherical outer articulation surface for articulating with an acetabulum and an inner surface, a longitudinal axis, an inferior aperture and a superior apex;
   a liner matable with the inner surface of the shell in proximity to the superior apex of the shell and having a spherical inner articulation surface for articulating with a prosthetic femoral head; and
   a locking liner element disposed within the shell and matable with the inner surface of the shell in proximity to the inferior aperture, the locking liner element including at least one resilient locking element integral therewith and extending from a region proximate to the inferior aperture of the shell inward toward the longitudinal axis of the shell and at least partially in a superior direction toward the apex of the shell, the resilient locking element being deformable, in response to an insertion force directed from the inferior aperture, from a first position, defining a first nominal diameter, outward away from the longitudinal axis of the shell to define a second, larger diameter, the locking liner element further comprising a groove formed in the locking liner element adjacent to a superior surface of the at least one resilient locking element, the groove providing clearance for the resilient locking element to deform in response to an insertion force directed from the inferior aperture;

wherein the locking liner element has a superior surface that abuts an inferior surface of the liner and the locking liner element includes an inferior facing surface that abuts a superior facing surface formed in the inner surface of the shell to hold the locking liner element against inferior movement with respect to the shell.

2. The prosthesis of claim 1, wherein the resilient locking element returns to its first position upon removal of the insertion force.

3. The prosthesis of claim 1, wherein the at least one locking element extends around a perimeter of the aperture.

4. The prosthesis of claim 3, wherein the groove extends around the perimeter of the aperture.

5. The prosthesis of claim 4, wherein at least one longitudinal groove is formed in the at least one locking element.

6. The prosthesis of claim 5, wherein the at least one locking element has a spherical surface portion that, when the at least one locking element is in its first position, defines a surface portion on a projection of the spherical inner surface of the liner.

7. The prosthesis of claim 1, wherein the spherical inner surface of the liner covers no more than one half of a sphere.

8. The prosthesis of claim 1, wherein a diameter of the spherical outer surface of the shell is between about 36 and 80 millimeters.

9. The prosthesis of claim 1, wherein the locking element is made from ultra high molecular weight polyethylene.

10. The prosthesis of claim 9, wherein the shell is made from a metal.

11. The prosthesis of claim 1, wherein the articulating prosthesis is a bipolar, hemiarthroplasty hip prosthesis.

12. The prosthesis of claim 11, wherein the spherical outer surface of the shell is adapted to articulate with an acetabulum.

13. The prosthesis of claim 11, further comprising a stem matabale with a femur.

14. The prosthesis of claim 11, wherein reinsertion of the femoral head into the shell following subluxation of the femoral head from the shell after installation of the prosthesis within a patient may be performed without surgery.

15. An articulating prosthesis comprising:
a shell having a spherical outer articulation surface for articulating with an acetabulum and an inner surface, a longitudinal axis, an inferior aperture and a superior apex;
a liner matable with the inner surface of the shell in proximity to the superior apex of the shell and having a spherical inner articulation surface for articulating with a prosthetic femoral head; and
a locking liner element disposed within the shell and matable with the inner surface of the shell in proximity to the inferior aperture, the locking liner element including at least one resilient locking element integral therewith and extending from a region proximate to the inferior aperture of the shell inward toward the longitudinal axis of the shell and at least partially in a superior direction toward the apex of the shell, the resilient locking element is deformable, in response to an insertion force directed from the inferior aperture, from a first position, defining a first nominal diameter, outward away from the longitudinal axis of the shell to define a second, larger diameter and returns to its first position upon removal of the insertion force, the locking liner element further comprising a groove formed in the locking liner element, adjacent to a superior surface of the at least one resilient locking element the groove providing clearance for the resilient locking element to deform in response to an insertion force directed from the inferior aperture; and
a stem member having a spherical head adapted to fit within and to articulate with the spherical inner surface of the liner;
wherein the locking liner element has a superior surface that abuts an inferior surface of the liner and the locking liner element includes an inferior facing surface that abuts a superior facing surface formed in the inner surface of the shell to hold the locking liner element against inferior movement with respect to the shell; and
wherein the spherical head is sized so as to deform the locking element from its first position to its second position in response to an insertion force applied to the spherical head from an inferior direction, allowing the spherical head to pass through the second, larger diameter of the locking element and to articulatably engage the spherical inner surface of the liner, the spherical head further being sized so as to allow the resilient locking element to return to its first, nominal diameter after the spherical head has engaged the inner surface of the liner.

16. The prosthesis of claim 15, wherein the at least one locking element extends around a perimeter of the aperture.

17. The prosthesis of claim 16, wherein the groove extends around the perimeter of the aperture.

18. The prosthesis of claim 16, wherein at least one longitudinal groove is formed in the at least one locking element.

19. The prosthesis of claim 15, wherein the spherical head has a diameter that is substantially equal to a diameter of the spherical inner surface of the liner, the value of each diameter being between about 22 and 32 millimeters.

20. The prosthesis of claim 15, wherein a diameter of the spherical outer surface of the shell is between about 36 and 80 millimeters.

21. The prosthesis of claim 15, wherein the locking element is made from ultra high molecular weight polyethylene.

22. The prosthesis of claim 21, wherein the shell is made from a metal.

* * * * *